United States Patent [19]

Krikorian

[11] Patent Number: 4,541,417
[45] Date of Patent: Sep. 17, 1985

[54] CORONARY AUGMENTER

[76] Inventor: Paul P. Krikorian, Spring Valley Rd., Morristown, N.J. 07960

[21] Appl. No.: 385,471

[22] Filed: Jun. 7, 1982

[51] Int. Cl.⁴ .............................................. A61B 5/04
[52] U.S. Cl. .................................. 128/1 D; 128/696
[58] Field of Search ............ 128/419 R, 419 F, 419 P, 128/419 PG, 419 D, 419 C, 419 W, 696, 702, 765, 421, 422, 423, 1 D, 695, 708, 419 G

[56] References Cited

U.S. PATENT DOCUMENTS

| | | | |
|---|---|---|---|
| 2,532,788 | 12/1950 | Sarnoff | 128/419 G |
| 3,750,644 | 8/1973 | Ragsdale | 128/1 D |
| 3,954,100 | 5/1976 | Sem-Jacobsen | 128/639 |
| 4,094,309 | 6/1978 | Grzenia | 128/644 |
| 4,147,171 | 4/1979 | Greene et al. | 128/421 |
| 4,153,049 | 5/1979 | Gatzke | 28/419 D |
| 4,202,340 | 5/1980 | Langer et al. | 128/419 D |
| 4,266,533 | 5/1981 | Ryaby et al. | 128/421 X |
| 4,295,474 | 10/1981 | Fischell | 128/697 |
| 4,303,075 | 12/1981 | Heilman | 128/419 D |
| 4,453,537 | 6/1984 | Spitzer | 128/1 D |
| 4,453,547 | 6/1984 | Castel et al. | 128/421 |

OTHER PUBLICATIONS

Radio-Electronics, vol. 36, No. 6, Jun. 1965, p. 29, "Electronics and the Aged".
Annals of Biomedical Engineering, vol. 8, No. 4-6, pp. 445-458, (1980), "The Principle of Electrical Carotid Sinus Nerve Stimulation: A nerve pacemaker system for angina pectoris and hypertension therapy".

*Primary Examiner*—Kyle L. Howell
*Assistant Examiner*—Francis J. Jaworski
*Attorney, Agent, or Firm*—Eric P. Schellin

[57] ABSTRACT

A coronary augmenter can affect blood flow in a patient. The augmenter has a timer and a stimulator. The timer can repetitively produce a trigger signal. The stimulator can repetitively apply to the patient a stimulating current sized to involuntary contract and relax at least one muscle of the patient in response to the trigger signal.

12 Claims, 6 Drawing Figures

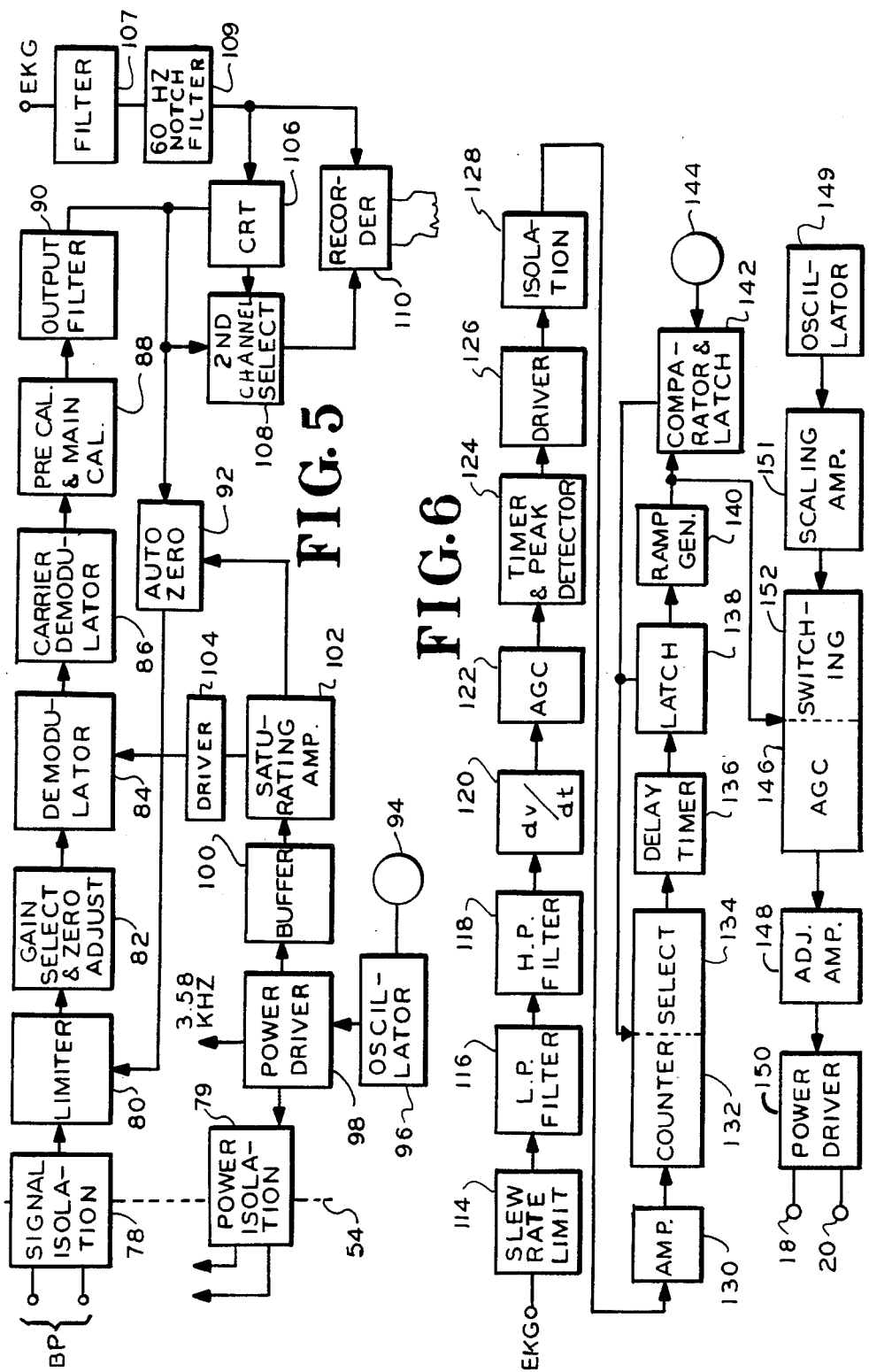

CORONARY AUGMENTER

BACKGROUND OF THE INVENTION

The present invention relates to coronary augmenters and, in particular, to systems for contracting skeletal muscles to affect blood flow and cardiac health in a cardiac patient and prevention of coronary artery disease in normal or high risk groups.

It is known to apply a tetanizing current across skeletal muscles of a patient who may be suffering from ailments such as tendonitis, neuritis, bursitis, or other muscle ailments. This therapy involves applying an alternating current across the muscle to contract it involuntarily for a predetermined interval, for example, five (5) minutes. However, this type of instrument has not been used nor proposed as a device for treating coronary disease.

It is also known that properly scaled exercise can affect the health of the heart. Research has also shown that exercise at an appropriate level can cause natural production by the body of sympathomimetic amines such as catecholamines. These catecholamines when placed into circulation can increase the contracting strength of muscles and dilate blood vessels supplying these muscles.

Various devices and appliances have been proposed for assisting a weakened myocardium. Such coronary augmenters have been disclosed in the literature; for example Hauser and Carleton, *The Failing Myocardium*, Symposium on Coronary Heart Disease, Medical Clinics of North America, Vol. 57, No. 1, January, 1973, at pp. 187–204; Giron, *Rationale and Early Experience in Assisted Circulation*, Department of Surgery, The Bronx Veterans Administration Hospital, Bronx, N.Y., 10468, at pp. 160–167; Weber at. al., *An Assessment of Intra-Aortic Balloon Pumping in Hypovolemic and Ischemic Heart Preparations*, The Journal of Thoracic and Cardiovascular Surgery, Vol. 64, No. 6, December 1972, at pp. 869–877. These references also disclose counterpulsation techniques for mechanically assisting the left ventricle. One known method involves an intra-aortic balloon which is inserted as a catheter into the femoral artery and routed into the aorta near the left ventricle. A pulsating source of pressurized carbon dioxide is used to quickly inflate and deflate the intra-aortic balloon. This repetitive action is triggered by an electrocardiac signal taken from the patient in a fashion similar to a standard electrocardiogram. This intra-aortic balloon is deflated during systole to relieve back pressure and to prevent the pump from working against the heart. During diastole, the balloon is reinflated thereby assisting the pumping action of the heart and also causing a back pressure tending to drive blood into the coronary arteries.

The literature has suggested that the myocardium has a capacity to bypass occluded coronary arteries by developing collateral circulation. The higher pressure heads caused by occluded arteries diverts blood through minor vessels and capillaries which consequently expand to provide a secondary bypass. Discussion of this phenomenon can be found in: Levin et. al., *Coronary Collateral Circulation and Distal Coronary Run-Off*, The American Journal of Roentgenology, Radium Therapy and Nuclear Medicine, Vol. 119, No. 3, November 1973, at pp. 463–473; Baroldi and Scomazzoni, *Coronary Circulation in Normal and Pathological Heart*, Office of Surgeon General, Department of Army, Washington, D.C., 1967; Knobel et. al., *Myocardial Blood Flow in Coronary Artery Disease*, Circulation, Vol. 47, April 1973, at pp. 690–696.

Another method of diastolic augmentation which is non-invasive employs a hydraulic boot in the form of a box surrounding the lower extremities of the patient. A bladder surrounding the extremities is inflated and deflated at a rate proportional to heartbeat. However, this method requires a relatively large hydraulic device having the disadvantages of being slow, heavy, and expensive. It is also a purely mechanical technique which does not at all involve body chemistry in the therapeutic treatment of the ailing myocardium.

Also, significant research has been undertaken to determine the effect of the phasing of inspiration and expiration on the heart. It has been suggested that proper phasing can increase the efficiency of the heart. Accordingly, research has been conducted to determine the effect of such respiratory phasing and also the effect of breathing apnea and respiratory paralysis from any cause. See for example, Horvat et. al., *Effect of Oxygen Breathing on Pacing-Induced Angina Pectoris and Other Manifestations of Coronary Inefficiency*, Circulation, Vol. 45, 1972, at p. 837; Pigott and Spodick, *Effects of Normal Breathing and Expiratory Apnea on Duration of the Phases of Cardiac Systole*, American Heart Journal, Vol. 82, No. 6, December, 1971, at pp. 786–793. Furthermore, this relative phasing of respiration has been considered important for a heart-lung machine. Also, research has been conducted to effect involuntary diaphragm contraction and pace respiration by means of stimulation to the phrenic nerve of a patient.

Accordingly, there is a need for apparatus and methods to treat and assist a diseased heart either in grave cases to sustain life or on a regular basis for normal patients interested in weight control, exercise and its therapeutic value. Such equipment and methods should be simple, effective, safe and sufficiently flexible to be used on various patients.

SUMMARY OF THE INVENTION

In accordance with the illustrative embodiment demonstrating features and advantages of the present invention, there is provided a coronary augmenter for affecting blood flow in a patient. The augmenter comprises timing means for repetitively producing a trigger signal. The augmenter also includes a stimulating means for repetitively applying to the patient a stimulating current. This current is sized to involuntarily contract and relax at least one muscle of the patient in response to the trigger signal.

A method according to the same invention can affect blood flow in a cardiac patient. This method includes the step of repetitively and involuntarily contracting and relaxing a muscle of the patient at a predetermined repetition rate.

In a preferred embodiment, some of the skeletal muscles of the patient are involuntarily contracted during diastole to provide several benefits. For one, the body responds to this involuntary exercise to produce sympathomimetic substances such as natural catecholamines. These catecholamines when induced into circulation can increase the strength of contraction of the myocardium during left ventricular contraction. In fact, these sympathomimetics can dilate coronary blood vessels and thereby increase the blood supply to and the efficiency of the myocardium. Secondly, the involuntary contraction of the skeletal muscles can be phased to produce back pressure during diastole. This is a form of counter-pulsation for increasing the venous return to the heart and for increasing arterial blood flow into the coronary arteries. In addition, since preferably the skeletal muscles relax during systole, the back pressure seen by the left ventricle is subsequently reduced thereby reducing the load on the heart.

In a particularly preferred embodiment, the timing of the contraction of the skeletal muscles is regulated by an electrocardiac sensor similar to an electrocardiogram. From the QRS complex an R pulse is developed indicating the onset of systole and after a predetermined delay the skeletal muscles are involuntarily contracted during diastole. In this preferred embodiment, the extent of the delay can be adjusted. Furthermore, the contractions can be set to occur either on every heartbeat or the second, third or other number. Also, the form of the tetanizing pulse causing the involuntary contraction can be an alternating signal which increases in amplitude and/or is unbalanced in amplitude so that one polarity is constant in amplitude while the other polarity can be either constant or increasing in amplitude.

Also in another embodiment, the R pulse can be used to operate a phrenic nerve stimulator. This stimulator is connected to a patient's phrenic nerve so that the diaphragm can be involuntarily contracted to pace respiration. Again, this respiration can be phased to occur on every heartbeat or, optionally, after every fourth or fifth heartbeat.

In a preferred embodiment, the tetanizing current is applied to the patient by means of a conductive mesh contained in a cloth tube soaked in an electrolyte. This type of contact is diffuse and avoids high current densities that may be uncomfortable for the patient.

It has been found upon experiments with dogs that apparatus according to the foregoing principles can produce a marked increase in the rate of change of pressure in the left ventricle during systole. Therefore the apparatus can cause a marked increase in the strength of myocardial contraction.

For a human patient on a heart-lung machine the apparatus can reinstate the pulsatile blood flow, normally reduced by the heart bypassing, thereby improving perfusion of vital organs.

It is further expected that the splanchnic pool of blood is mobilized by the foregoing apparatus due to abdominal muscle contraction. Also the foregoing apparatus can provide a form of artificial exercise not only improving the health of the heart but also possibly controlling weight in normal people.

BRIEF DESCRIPTION OF THE DRAWINGS

The above brief description as well as other objects, features and advantages of the present invention will be more fully appreciated by reference to the following detailed description of the presently preferred but nonetheless illustrative embodiment in accordance with the present invention when taken in conjunction with the accompanying drawings wherein:

FIG. 5 is a block diagram showing in further detail the blood pressure transducer and display apparatus of FIG. 1; and FIG. 6 is a block diagram showing in further detail the tetanizing trigger and control of FIG. 1.

DETAILED DESCRIPTION OF THE PREFERRED EMBODIMENT

Figure 1:
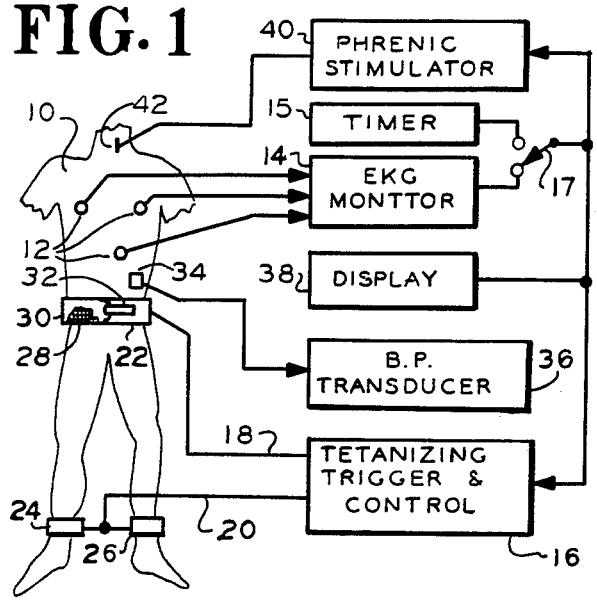
FIG. 1 is a schematic block diagram showing an augmenter according to the principles of the present invention.

Referring to FIG. 1, a coronary augmenter is shown herein connected to a human cardiac patient 10 through monitoring electrodes, in the form of conventional electrocardiogram electrodes 12. Electrodes 12 connect to a timing means shown herein as an electrocardiac sensing means 14. As explained hereinafter in further detail, sensing means 14 has circuitry similar to that found in an electrocardiogram-type of system. An alternate sensing means is shown herein as timer 15 which produces a pulse at a rate which may be equivalent to the expected heartbeat of patient 10. The output of either timer 15 or electrocardiac monitor 14 can be selected by means of switch 17.

Figure 2:
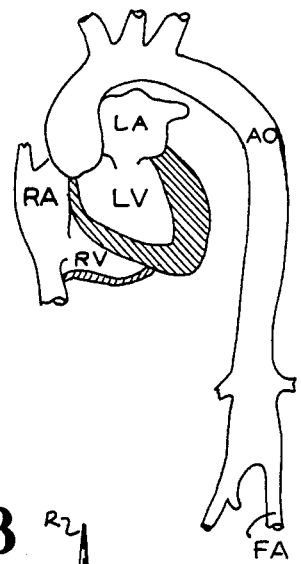
FIG. 2 is a sectional diagram of the human heart.

Referring to FIG. 2, the human heart, illustrated in section, comprises a left atrium LA feeding a left ventricle LV which ultimately supplies blood to aorta AO. Upon electrical stimulation, the myocardium associated with left ventricle LV contracts causing an ejection of blood from left ventricle LV into aorta AO to supply blood to vital organs and muscles of the body. In particular, the leg muscles are supplied by femoral artery FA. The elastic recoil of the aortic arch forces some of the arterial blood back into the opening of the right and left coronary arteries at their origin in the cusps of the aortic valves. It is primarily after the closing of this valve, an interval referred to as diastole, that blood is supplied to the myocardium through the associated coronary arteries.

The onset of systole can be electrically detected by the QRS complex, as shown in FIG. 3a as the R pulse. This R pulse signifies the electrical stimulation causing contraction of the left ventricle at the onset of systole. Systole is indicated in FIG. 3a as interval SS. The end of systole is indicated by the T wave signifying ventricular repolarization. The following contraction of the left atrium is indicated by the P wave also illustrated in FIG. 3a.

Referring again to FIG. 1, a stimulating means is shown herein as tetanizing trigger and control system 16. The timing for system 16 is provided from electrocardiac monitor 14 or timer 15 depending on the position of switch 17. In response to the periodic signals from switch 17, system 16 provides a tetanizing current on line 18 and 20. In this embodiment, the tetanizing current is applied from band 22 to bands 24 and 26. Band 22 is a waist band having an internal conductor in the form of mesh 28. Mesh 28 is covered by an electrolyte-absorbent cover 30 in the form of a cloth tube. In this embodiment, band 22 is secured by a Velcro TM strap 32, although obviously other fasteners are possible. Bands 24 and 26 are similar to band 22 but are sized to fit the ankles or lower thighs of patient 10. Bands 24 and 26 are connected together to line 20 so the two ankles are held at the same potential. Being connected in this fashion, major skeletal muscles are affected, including the calf, thigh, gluteus maximus and lower back muscles.

Figure 3:
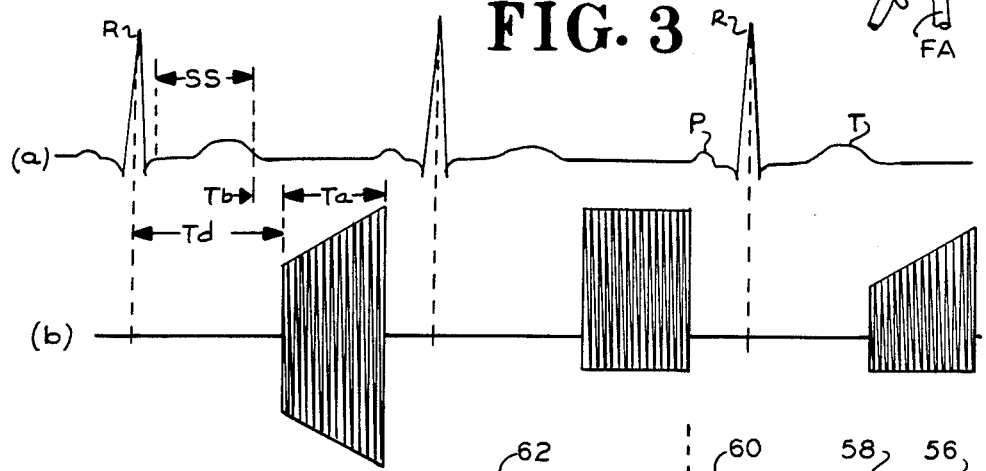
FIG. 3 is a pair of timing diagrams showing electrical signals associated with the apparatus of FIG. 1.

The waveforms and timing of various tetanizing current pulses are illustrated in FIG. 3. In FIGS. 3a and 3b a different tetanizing pulse Ta is shown occurring after each R pulse. However, it is expected that for some embodiments, a tetanizing pulse will occur only after every second or third (or other number) R pulse. Furthermore, while the three tetanizing pulses of FIG. 3b each have different amplitude envelopes, in most embodiments, the envelope for successive pulses will be the same.

The tetanizing pulses of FIGS. 3b are shown occurring after a delay interval Td after the production of the R pulse. This delay Td is sufficient to commence the tetanizing pulse with a delay Td after the end of systole interval SS. The tetanizing current pulse has a duration Ta which terminates before the end of diastole (that is, before systole).

The pulses of FIG. 3b are three examples of preferred amplitude envelopes. The envelopes encompass a voltage waveform, preferably alternating at 400 Hertz. The first such envelope is symmetrical with respect to the zero amplitude reference but has an amplitude that linearly increases from an initial moderate value to a final maximum value over the interval Ta. The second exemplary envelope is shown as an unbalanced square envelope. Accordingly, its peak excursions in the positive direction are equal but exceed the equal excursions in the negative direction. The third illustrated envelope is a combination of the first two. Its positive excursions are the same as that shown for the first envelope while its negative excursions are the same as that of the second.

Referring again to FIG. 1, an optional blood pressure transducer 34 is shown implanted into patient 10. Transducer 34 is in the form of a catheter that is inserted into the femoral artery (artery FA of FIG. 2). Transducer 34 connects to sensing transducer electronics 36 to process the signals of transducer 34 and convey them to display 38. As described further hereinafter, display 38 comprises a cathode ray tube together with a strip chart recorder. Another input to display 38 is the output of switch 17, normally the electrocardiac signal produced by electrocardiac monitor 14. Also an optional connection can be switched to observe the stimulating voltage waveform concurrently with the EKG tracing.

Another optional accessory, phrenic stimulator 40, acts as a stimulating means responsive to the electrocardiac signals through switch 17 from monitor 14 (or timer 15). Phrenic stimulator 40 produces an output signal which is applied to the phrenic nerve 42 of patient 10. The connection to the phrenic nerve may be performed in accordance with the procedure disclosed in Glenn, W. L., et. al., *Diaphragm Pacing by Radio Frequency Transmission in the Treatment of Chronic Ventilatory Insufficiency*, The Journal of Thoracic and Cardiovascular Surgery, Volume 66, No. 4, October, 1973, at pp. 505-511.

Figure 4:
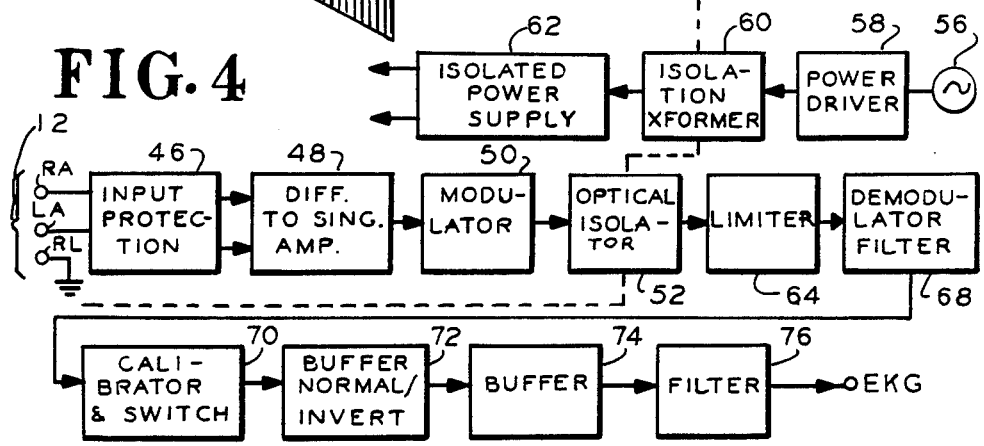
FIG. 4 is a block diagram showing in further detail the electrocardiac monitor of FIG. 1.

Referring to FIG. 4, previously illustrated input electrodes 12 are separately identified as electrodes RA, LA and ground terminal RL. Inputs RA and LA are applied to a diode clamping or similar circuit to protect these inputs from excessive voltages which may be inadvertently applied to terminals 12. The inputs 12 are applied to differential amplifier 48. The output of amplifier 48, a relatively low frequency signal, is applied to modulator 50 to modulate the signal by chopping (alternatively amplitude, frequency or other modulation can be performed). This modulated output is then conveyed through optical isolator 52 which, in this embodiment, is a light emitting diode optically coupled to a photoelectric transistor. Boundary 54 is shown as an isolation boundary eliminating direct leakage currents or ground loops from the other circuitry from reaching terminals secured to the patient. To power elements 46-52, a 60 cycle source 56 powers driver 58 to produce a higher frequency, for example, 3.58 kHz. This higher frequency output can be coupled through toroidal isolation transformer 60 to drive power supply 62. Accordingly, the output of isolation transformer 60 does not have a direct connection to power source 56. Power supply 62 in a conventional fashion converts the alternating currents conveyed through transformer 60 into the appropriate direct current potentials.

The output of optical isolator 52 is coupled through a limiter 64, which can include a diode clamp or similar device that clips excessively high voltage excursions associated typically with noise. This limited signal from limiter 64 is then demodulated and filtered in demodulator 68, which can be in its simplest form a diode demodulator operating through a capacitive filter. Of course, other forms of demodulation may be appropriate, including synchronous demodulation. The output of demodulator 68 is fed through switched calibrator 70. Calibrator 70 is essentially a device which either couples the output of demodulator 68 directly through or substitutes a calibrated standard having a precisely regulated amplitude. This substituted calibration signal is useful in measuring and correlating the responses of the various systems downstream of switch calibrator 70. The output of switch calibrator 70 is fed through buffer amplifier 72 which can be switched to provide an output signal in phase or inverted with respect to its input. Another buffer amplifier 74 driven by buffer 72 is coupled through a bandpass, noise limiting filter 76 to provide an output on terminal EKG. The signal on terminal EKG will be normally in the form illustrated in FIG. 3a.

Referring to FIG. 5, the blood pressure transducer and display system (elements 36 and 38 of FIG. 1) are illustrated in block form. The output of the blood pressure transducer is identified herein as terminal pair BP which connect to signal isolation circuit 78, a circuit employing optical isolation similar to isolator 52 (FIG. 4). However the power for the transducer and isolator, is a 3.58 kHz signal from supply 79 providing alternating power. Therefore the transducer signal is modulated by a carrier at the same rate. The output of isolation circuit 78 is coupled through an offsettable limiter 80 to feed a gain select and zero adjust circuit 82. Circuit 82 employs an amplifier having a variable gain and offset so that the scaling of signals can be adjusted. Since the signals produced by the foregoing components are modulated, they are coupled through demodulators 84 and 86 which act as synchronous demodulators. As explained hereinafter the carrier for the transducer is derived from the 3.58 kHz signal from supply 79 and is applied to demodulator 84 to effect synchronous demodulation. Calibration circuit 88, driven by demodulator 86, is operable to either transfer to output filter 90 the output of demodulator 86 or to substitute therefore a square wave signal having a predetermined, precise amplitude. The output of filter 90 is fed back through auto-zero circuit 92. Auto zero circuit 92 is operable when the output from supply 79 is zero to return a biasing signal to limiter 80 sized to produce a zero output from filter 90.

This biasing signal is thereafter held capacitively or otherwise to correct offsets automatically. Power is delivered to supply 79 from a main power source 94.

Source 94 powers oscillator 96 to operate power driver 98 at 3.58 kHz. This 3.58 kHz signal is conveyed through a toroidal isolation transformer in supply 79 to provide to isolation circuit 78 on the patient's side of boundary 54 the previously described power signal. The 3.58 kHz power signal of driver 98 is also coupled through buffer 100 to saturating amplifier 102. Amplifier 102 rapidly saturates and applies a synchronous square wave through, driver 104 to demodulator 84. Accordingly, since the carrier derived from the 3.58 kHz power signal applied to signal isolation circuit 78 by supply 79 is synchronous with the output from driver 104, demodulator 84 can provide synchronous demodulation.

The blood pressure information from filter 90 is supplied to cathode ray tube 106 together with electrocardiac signals from terminal EKG, filtered through noise filter 107 and 60 Hz notch filter 109. Cathode ray tube 106 may be a dual-trace scope for simultaneously showing the output signals coupled thereto. Also the blood pressure information from filter 90 is coupled to a second channel selector 108 so that blood pressure data can be switched into recorder 110. Recorder 110 may also be a dual channel recorder so that the blood pressure signals and the electrocardiac signals from terminal EKG can be simultaneously recorded on a strip chart.

Referring to FIG. 6, the tetanizing trigger and control circuit (circuit 16 of FIG. 1) is shown herein in block diagram form wherein the electrocardiac signal of terminal EKG is applied to slew rate limiting circuit 114. Circuit 114 is designed to allow only a limited rate of change. This feature eliminates excessive high frequency noise in the system. The output of circuit 114 is coupled through cascaded low pass filter 116 and high pass filter 118 to provide bandpass filtering. The output of high pass filter 118 is applied to differentiator 120 which drives an automatic gain control 122. In a conventional fashion, automatic gain control 122 responds to the signal from differentiator 120 to keep its magnitude above a certain amplitude. The output of gain control circuit 122 drives delayed peak detector 124 to provde a minimum delay. This delay is chosen so that the R wave (FIG. 3a) applied at terminal EKG is not coupled through to driver 126 until after the end of systole. This significant feature avoids stressing the heart by counterpulsing the blood pressure during systole when the valve from the left ventricle is open. Driver 126 is coupled through an isolation circuit 128 to provide an output to a fixed gain amplifier 130. Amplifier 130 drives a counter 132 having a section 134 for selecting the factor by which the incoming pulses from amplifier 130 are divided. Division by a factor of 1, 2, 3, 4, 5 or any other suitable number may be appropriate depending upon the circumstances. The divided pulse from counter 132, 134 drives optional variable delay timer 136. Timer 136 can be used to precisely position tetanizing current pulses with respect to the R pulse. The pulse produced from timer 136 is used to set a latch 138 which remains in a high state until reset. The high state of latch 138 enables ramp generator 140 to produce a signal that linearly increases in time. This linearly increasing signal from generator 140 is applied to one input of comparator/latch 142 whose other input is tied to a reference potential from source 144. Comparator 142 produces a signal which remains fixed for a period of time depending upon the magnitude of reference voltage 144. When ramp generator 140 exceeds in magnitude the output of source 144, comparator 142 resets latch 138 and counter 132. Accordingly, ramp generator 140 produces a triangular wave on a duty cycle established by the count selected at count selector 134. This triangular wave is connected to gain control circuit 146 to vary its gain, as explained hereinafter.

The input to gain control circuit 146, a 400 Hz signal, is derived from oscillator 149 through a scaling amplifier 151. Switching circuit 152, a portion of circuit 146, is an active, variable resistance circuit for continuously varying the gain of circuit 146 according to the output of ramp generator 140. The gain control circuit 146 adjusts the amplitude of the 400 Hz signal from oscillator 149 so it increases with time. The output of control circuit 146 is applied to amplifier 148 which in some embodiments may include a clipper for limiting the amplitude in the negative, positive, or both half cycles. The signal of amplifier 148 is applied to power driver 150 to produce on terminals 18 and 20 the tetanizing current previously described in connection with FIG. 3b.

In order to facilitate an understanding of the principles associated with the foregoing apparatus, its operation will be briefly described. Cardiac patient 10 (FIG. 1) is initially placed in a relaxed, recumbent position and electrocardiac terminals 12 are secured to the chest of a patient in the usual fashion, for example, with self-adherent electrodes. The patient is also fitted with tetanizing electrodes 22, 24 and 26 soaked with a polar solution such as alcohol. The electrodes are secured appropriately, for example, band 22 is secured around the waist of patient 10 by tightening strap 32. The connection of FIG. 1 effectively places the thigh, calf and gluteus maximus muscles of patient 10 in circuit between leads 18 and 20.

The operator may also wish to monitor the blood pressure of the patient. To this end, catheter-type transducer 34 is inserted into femoral artery FA of the patient (FIG. 2). As will be appreciated from FIG. 2 the pressure at the femoral artery is about the same as that in the upper aorta. In the event that the patient suffers from a respiratory disorder, a physician can, in a known manner, surgically expose a phrenic nerve in the neck of patient 10 and place a conductive cuff around that nerve 42. Stimulation of phrenic nerve 42 can cause involuntary contraction of the diaphragm muscles controlling respiration.

Before enabling the tetanizing current of system 16 (FIG. 1) the operator may wish to calibrate the various signals. To this end, a switch (not shown) associated with calibrator 70 (FIG. 4) can be momentarily depressed to apply a 1 milivolt signal to terminal EKG. The voltage on terminal EKG is then displayed on screen 106 and/or recorder 110. Accordingly, the gain adjustment associated with those instruments can be adjusted so the voltage as displayed will be calibrated to permit direct measurement on the display devices. Similarly, calibration circuit 88 (FIG. 5) can be actuated so that a predetermined square wave is applied to the display devices 106 and 110. These calibrated signals are again used to allow gain adjustment at the display devices so that subsequent signals can be read directly.

Delay circuit 136 can now be adjusted. In a preferred embodiment, variable adjustment is effected through two delay ranges: 0.5 to 100 miliseconds and 5 to 1000 miliseconds (from R pulse). Also, buffer 72 may be inverted to display the electrocardiac signals in the conventional manner. Next, counter select 134 can be adjusted to produce tetanizing pulses on every other heartbeat (as indicated by the R wave) or on any second, third, fourth or fifth R pulse (or any other number). Also the duration of the tetanizing pulse can be established by adjusting the magnitude of reference voltage 144 or the rate of generator 140. Finally, amplifier 148 is adjusted to establish the magnitude of current applied to the patient along terminals 18 and 20.

At this time, the power driver 150 can be enabled and, preferably, the tetanizing current gradually increased to the desired level within about 2 minutes, either manually or through automatic initiating circuitry (not shown). The tetanizing current may take one of the forms illustrated in FIG. 3b. The next occurring R pulse is applied by the circuit of FIG. 4 to terminal EKG and thence to counter 132 (FIG. 6). Counter 132 will count, for example, three R pulses before a pulse is applied to delay timer 136. Delay timer 136 does not respond to the pulse from counter 132 until after its internal timing mechanism has indicated the appropriate amount of time has elapsed. The elapsed time assures that systole has also elapsed. Thereafter, latch 138 is set so that generator 140 commences to ramp upwardly towards a magnitude established by reference voltage 144. As the output of ramp generator 140 increases, gain control circuit 146 conveys the signal from oscillator 149 to power driver 150 but at a ramping amplitude. As a result, a 400 Hertz signal varying typically from 20 to 100 volts in amplitude and preferably having a sinusoidal wave shape is applied to the patient across terminals 18 and 20. In response, the skeletal muscles of patient 10 from band 22 to bands 24 and 26 contract. This contraction sequence is diagramatically illustrated in FIG. 3. The contraction occurs during interval Ta which commences with a delay Td after the R wave and a delay Tb after the end of systole interval SS. Being timed in this fashion, the muscle contraction occurs during a period when the left ventricle is closed to the aorta. This results in a certain amount of counterpulsation which induces blood to flow into the coronary arteries and to increase the venous return. Also, when the tetanizing pulse ceases, the constriction in the blood vessels ceases so that the effective volume seen by the aorta (FIG. 2) increases. This is, in effect, pumping assistance to the heart. It is preferred that heartbeat rate be monitored throughout to avoid excessively high rates.

The tetanizing pulse ends when ramp generator 140 (FIG. 6) reaches the magnitude of reference potential 144. Comparator 142 then resets counter 132 and latch 138, causing generator 140 to reset.

Of importance is that the rhythmic contraction and relaxation of skeletal muscles naturally induces into circulation a sympathomimetic substance such as catecholamine. These substances can increase the strength of contraction of the myocardium and dilate some of the coronary arteries. This increases the strength of contraction in the left ventricle and produces a benefit similar to that of normal exercise. In one experiment with normal laboratory dogs, the cardiac output was increased from a baseline of 2.3 (reference) to 3.7 with 75 volts of stimulation. In this experiment the musculature was stimulated after every third or fourth heartbeat for 50 milliseconds duration with the stimulation occurring after a 200 millisecond delay from the beginning of diastole.

In the event the patient has a very weak electrocardiac signal, or in the event that the physician does not wish to trigger tetanizing current pulses from the heartbeat, switch 17 can be thrown from the position shown to connect timer 15 to control 16. Thereafter the repetition rate and duty cycle of the tetanizing pulses are determined by timer 15. Furthermore, in the event respiratory failure is a problem, the physician can actuate phrenic stimulator 40 to pace respiration at a fixed rate.

It is to be appreciated that various modifications may be implemented with respect to the above described preferred embodiment. For example, various blocks shown in the diagrams herein may be eliminated. In some embodiments the offsets, gains, signal levels and repetition rates may be standardized rather than being adjustable. Furthermore, some embodiments will not use any display devices. Also, while isolation is shown by means of photoelectric transistors or transformers, in some embodiments alternate means of isolation may be employed including hydraulic, pneumatic etc. In addition, various timing relationships, frequencies, amplitudes, repetition rates and other factors which have been described above may be altered depending upon the patient. Also, while specific types of modulation and demodulation have been disclosed, it will be understood that such modulation may be eliminated or alternate types of modulation may be employed instead. Also, the filtering, slew rate limiting, amplitude limiting and other signal processing techniques described herein may in some embodiments be eliminated or modified depending upon the types of signals and noise that are expected. In addition, while counters are shown for counting heartbeats, in some embodiments, the counter may be eliminated in favor of a timer which develops a blocking interval. Also it is expected that in some embodiments there will be no stimulation to the phrenic nerve and thus this associated equipment will not be included. Furthermore, in some embodiments, there will be no blood pressure transducers; which are included herein primarily for analysis.

Apparatus according to the principles of the present invention can augment coronary blood flow:

(a) by self application on a daily basis in high risk groups or for preventive reasons on healthy persons;

(b) during surgery or any procedures in people with poor coronary flow or compromised ventricular dynamics or valvular disease.

Such apparatus can also produce a more physiologic type of perfusion of vital organs, e.g. pulsatile instead of the steady state flow while a person is on a heart-lung machine. This apparatus can also exercise patients (electronically) while undergoing cardiac catheterization. Furthermore the phrenic nerve can be stimulated at the most beneficial part of and rate of the cardiac cycle. This would be an exception where invasion of the body would be required by the electrodes placed on the phrenic nerve. Conditions requiring invasion would be respiratory paralysis from any cause, sleep apnea etc. The apparatus can also be used where recumbent exercise with an increase in coronary blood flow, cardiac output and increase in left ventricular inotropy with minimal increase in total oxygen consumption would be beneficial. The apparatus herein disclosed will also be useful for congestive heart failure and/or valvular disease where cathetherization presents a high risk. The apparatus can be applied to a patient suffering from pulmonary edema or congestion to allow use of a cathether.

Obviously many modifications and variations of the present invention are possible in light of the above teachings. It is therefore to be understood that within the scope of the appended claims, the invention may be practiced otherwise than as specifically described.

What is claimed is:

1. A coronary blood flow augmenter for affecting blood flow in a patient, comprising:
   timing means for repetitively producing a trigger signal in response to a patient's heart beat; and
   stimulating means for repetitively applying to a patient a stimulating current size to involuntarily contract and relax at least one muscle in a patient in response to said trigger signal, and stimulating current being timed by said timing means to produce muscular contraction in a muscle excluding a heat during diastole.

2. A coronary blood flow augmenter according to claim 1 wherein said timing means is provided with a sensing means the actuate the timing means at a preselected repetition rate that is proportional to a heartbeat of a patient.

3. A coronary blood flow augmenter according to claim 2 where said stimulating means is provided with a means for controlling the duration of the stimulating current.

4. A coronary blood flow augmenter according to claim 3 wherein the sensing means comprises two monitoring electrodes externally secured to a patient to sense electrocardiac signals.

5. A coronary blood flow augmenter according to claim 4 wherein the electrocardiac signals of a patient have a repeating R-pulse corresponding to imminent systole, said stimulating means having a delay means for producing the stimulating current after a predetermined delay following the R-pulse.

6. A coronary blood flow augmenter according to claim 5 wherein said stimulating means is provided with a counter for counting the R-pulse whereby said stimulating means produces a stimulating current after the R-pulse is produced a predetermined number of times as counted by the counter.

7. A coronary blood flow augmenter according to claim 3 wherein said stimulating means is provided with a means for increasing the amplitude of the stimulating current with time.

8. A coronary blood flow augmenter according to claim 3 wherein said stimulating means comprises at least two stimulating electrodes adapted to be connected across a muscle of a patient.

9. A coronary blood flow augmenter according to claim 8 wherein said stimulating electrodes comprised two bands that are wrapped around a patient.

10. A coronary blood flow augmenter according to claim 9 wherein the two bands comprise two conductors with two electrolyte-absorbent covers.

11. A method of augmenting coronary blood flow in a patient, comprising the following steps:
    monitoring a heart beat of a patient;
    developing a repetitive trigger signal in response to a heart beat of a patient; and
    repetitively stimulating, by a stimulating current, at least one muscle in a patient to contract and relax in response to the trigger signal, whereby muscular contraction is produced in at least one muscle, excluding the heart, during diastole.

12. A method of augmenting coronary blood flow in a patient according to claim 11 comprising the additional steps of counting the trigger signal and activating the stimulating current in response to a preselected number of trigger signals.

* * * * *